United States Patent
Okada

(10) Patent No.: US 10,238,407 B2
(45) Date of Patent: Mar. 26, 2019

(54) BASKET-TYPE GRASPING FORCEPS

(71) Applicant: OLYMPUS CORPORATION, Hachioji-shi, Tokyo (JP)

(72) Inventor: Tsutomu Okada, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/400,781

(22) Filed: Jan. 6, 2017

(65) Prior Publication Data

US 2017/0112516 A1  Apr. 27, 2017

Related U.S. Application Data

(63) Continuation of application No. PCT/JP2015/078364, filed on Oct. 6, 2015.

(30) Foreign Application Priority Data

Oct. 7, 2014  (JP) .................................. 2014-206485

(51) Int. Cl.
  *A61B 17/221* (2006.01)
  *A61B 17/22* (2006.01)
  *A61B 17/00* (2006.01)

(52) U.S. Cl.
  CPC ...... *A61B 17/221* (2013.01); *A61B 17/22031* (2013.01); *A61B 2017/00477* (2013.01); (Continued)

(58) Field of Classification Search
  CPC .. A61B 17/221; A61B 2017/2212–2017/2217; A61B 2017/00358
  See application file for complete search history.

(56) References Cited

U.S. PATENT DOCUMENTS

| | | | | |
|---|---|---|---|---|
| 4,347,846 A | * | 9/1982 | Dormia | A61B 17/221 606/127 |
| 5,860,987 A | * | 1/1999 | Ratcliff | A61B 17/0218 606/110 |

(Continued)

FOREIGN PATENT DOCUMENTS

| | | |
|---|---|---|
| EP | 2 638 870 A1 | 9/2013 |
| JP | H02-116411 U | 9/1990 |

(Continued)

OTHER PUBLICATIONS

Dec. 28, 2015 International Search Report issued in PCT/JP2015/078364.

(Continued)

*Primary Examiner* — Darwin Erezo
*Assistant Examiner* — Jonathan Hollm
(74) *Attorney, Agent, or Firm* — Oliff PLC

(57) ABSTRACT

A binding part of a basket-type grasping forceps includes: a first binding part to which proximal ends of first wires that are some of a plurality of basket wires are fixed; and a second binding part to which proximal ends of second wires not connected to the first binding part among the plurality of basket wires are fixed, which is engaged with the first binding part to be separable from the first binding part, is containable inside a sheath along with the first binding part in a state in which the second binding part is engaged with the first binding part, and is held by an inner surface of the sheath to be inseparable from the first binding part in the sheath.

17 Claims, 9 Drawing Sheets

(52) U.S. Cl.
CPC ............... *A61B 2017/2212* (2013.01); *A61B 2017/22035* (2013.01)

(56) References Cited

U.S. PATENT DOCUMENTS

| | | | |
|---|---|---|---|
| 7,169,154 B1 | 1/2007 | Que et al. | |
| 8,118,816 B2* | 2/2012 | Teague | A61B 17/221 606/113 |
| 2004/0026942 A1* | 2/2004 | Kessler | A61B 17/221 294/100 |
| 2004/0116941 A1 | 6/2004 | Reynolds et al. | |
| 2004/0138677 A1 | 7/2004 | Little et al. | |
| 2005/0075648 A1* | 4/2005 | Komiya | A61B 17/221 606/127 |
| 2006/0100641 A1 | 5/2006 | Teague | |
| 2009/0082780 A1* | 3/2009 | Lu | A61B 17/221 606/127 |
| 2011/0028987 A1 | 2/2011 | Little et al. | |
| 2014/0012283 A1 | 1/2014 | Yasuda et al. | |

FOREIGN PATENT DOCUMENTS

| | | |
|---|---|---|
| JP | 2002-516139 A | 6/2002 |
| JP | 2003-530944 A | 10/2003 |
| JP | 2008-272501 A | 11/2008 |
| JP | 2015-123230 | 7/2015 |
| WO | 99/60933 A1 | 12/1999 |
| WO | 01/80748 A2 | 11/2001 |
| WO | 2012/141213 A1 | 10/2012 |
| WO | 2015/072366 A1 | 5/2015 |

OTHER PUBLICATIONS

Jun. 21, 2016 Office Action issued in Japanese Patent Application No. 2016-526256.

Jun. 1, 2018 Extended European Search Report issued in European Patent Application No. 15849611.7.

Dec. 29, 2018 Office Action issued in Chinese Patent Application No. 201580039686.8.

\* cited by examiner

BASKET-TYPE GRASPING FORCEPS

FIELD OF THE INVENTION

This application is a continuation application, based on PCT/JP2015/078364, filed on Oct. 6, 2015, claiming priority based on Japanese Patent Application No. 2014-206485, filed on Oct. 7, 2014, the content of which is incorporated herein by reference.

The present invention relates to a basket-type grasping forceps.

DESCRIPTION OF THE RELATED ART

Conventionally, a basket-type grasping forceps inserted into an intracorporeal duct such as a bile duct to collect a foreign object such as a calculus is known (for example, see Patent Documents 1 and 2).

Basket-type grasping forceps has a structure in which a foreign object is held by a plurality of wires. When a large foreign object is attempted to be collected using a basket-type grasping forceps, a basket cannot be removed from a duct while holding the foreign object. For example, when a foreign object is prevented from coming out of a space between the plurality of wires described in Patent PCT International Publication No. WO2012/141213 and U.S. Pat. No. 8118816, the basket cannot be removed from the duct.

SUMMARY OF THE INVENTION

Means for Solving the Problem

An aspect of the present invention provides a basket-type grasping forceps that includes: a sheath; a manipulating wire inserted into the sheath; a plurality of basket wires which is projected from a distal portion of the sheath and which forms a basket section configured to hold a target; a first binding part to which proximal end of at least one of the plurality of basket wires is fixed in a proximal side of the plurality of basket wires, and configured to be connected with the manipulation wire and move between inside of the sheath and outside of the sheath; and a second binding part to which proximal end of at least one of the basket wires which is different from the basket wire connected to the first binding part among the plurality of basket wires are fixed, which is capable of being held by the first binding part in the sheath, and which is capable of being released from the manipulating wire by separating from the first binding part in a state in which the second binding part is disposed outside of the sheath.

The basket section may include: a dense portion at which a plurality of basket wires are disposed in a spiral shape at an interval which enables capture of the target at a distal end side of the basket section; and a sparse portion at which the plurality of basket wires are disposed in a spiral shape at an interval which enables introduction of the target into the basket section at a proximal end side of the basket section.

The first binding part may have a distal engaging part disposed close to a distal end of the sheath than the distal end of the second binding part in a state in which the second binding part is in the sheath, having a first contact surface directed to a proximal side of the sheath such that the first contact surface is capable of engaging with the second binding part.

The first binding part may have a proximal engaging part disposed close to a proximal end of the sheath than the proximal end of the second binding part in a state in which the second binding part is in the sheath, having a second contact surface directed to a distal side of the sheath such that the second contact surface is capable of engaging with the second binding part.

The basket wires fixed to the first binding part among the plurality of basket wires may be arranged in a semicircular arc shape, and the basket wires fixed to the second binding part among the plurality of basket wires may be arranged in a semicircular arc shape.

The first binding part may be connected to the manipulating wire, and the second binding part may be configured to be separated from the manipulating wire when the second binding part is separated from the first binding part.

The basket-type grasping forceps may further include an adjusting mechanism configured to adjust an amount of forward/backward movement of the manipulating wire by switching between a state in which movement of the manipulating wire is restricted such that the first binding part and the second binding part move forward and backward in the sheath and a state in which the movement of the manipulating wire is allowed up to a position at which the first binding part and the second binding part are exposed outside the sheath.

The basket section may include a support member that is connected to distal ends of the plurality of basket wires and is at least partially inserted into the sheath.

The basket section includes: a dense portion at which a plurality of basket wires are disposed in a spiral shape at an interval which enables capture of the target at a distal end side of the basket section; and a sparse portion at which the plurality of basket wires are disposed in a spiral shape at an interval which enables introduction of the target into the basket section at a proximal end side of the basket section; and the support member may be disposed in the dense portion of the basket section at a position that is closer to the basket wires fixed to the first binding part among the plurality of basket wires than to the basket wires fixed to the second binding part among the plurality of basket wires

DETAILED DESCRIPTION OF THE INVENTION (First Embodiment)

Figure 1:
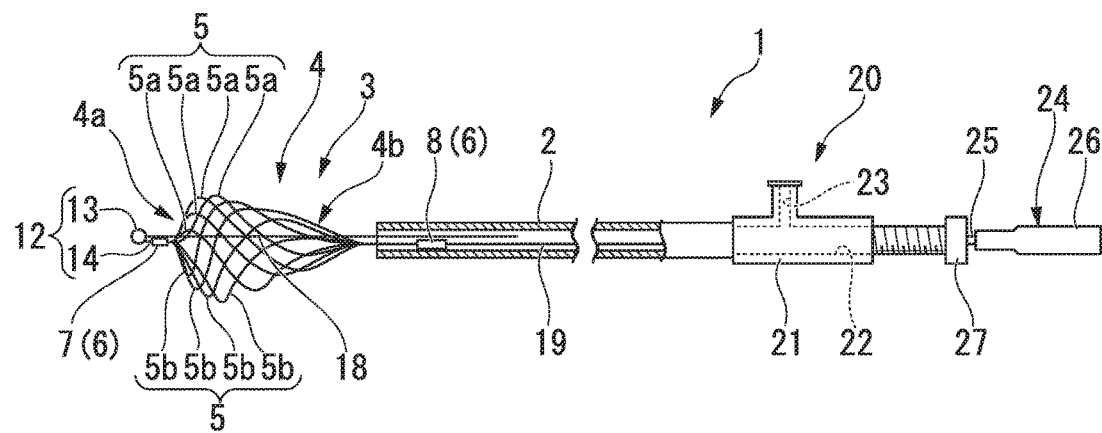
FIG. 1 is a partial cross-sectional view showing a basket-type grasping forceps of a first embodiment of the present invention.
Figure 2:
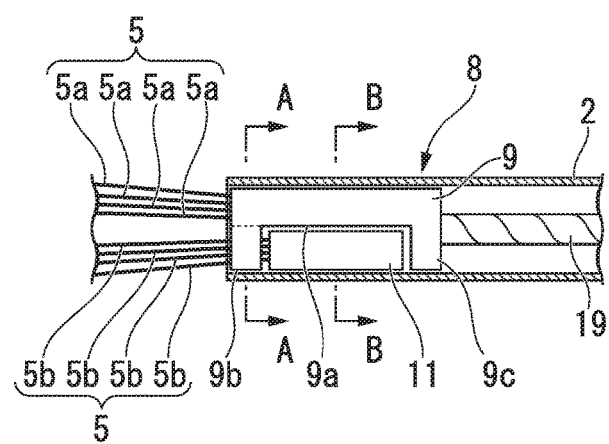
FIG. 2 is a side view showing a part of a basket section of the basket-type grasping forceps.
Figure 3:
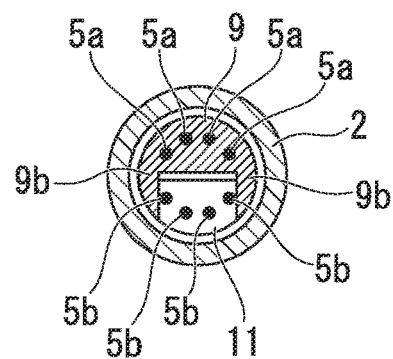
FIG. 3 is a cross-sectional view taken along line A-A of FIG. 2.
Figure 4:
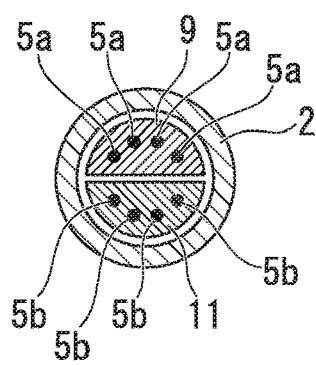
FIG. 4 is a cross-sectional view taken along line B-B of FIG. 2.
Figure 5:
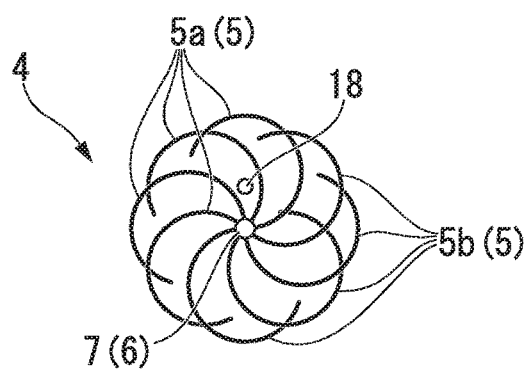
FIG. 5 is a front view showing a part of the basket section.
Figure 6:
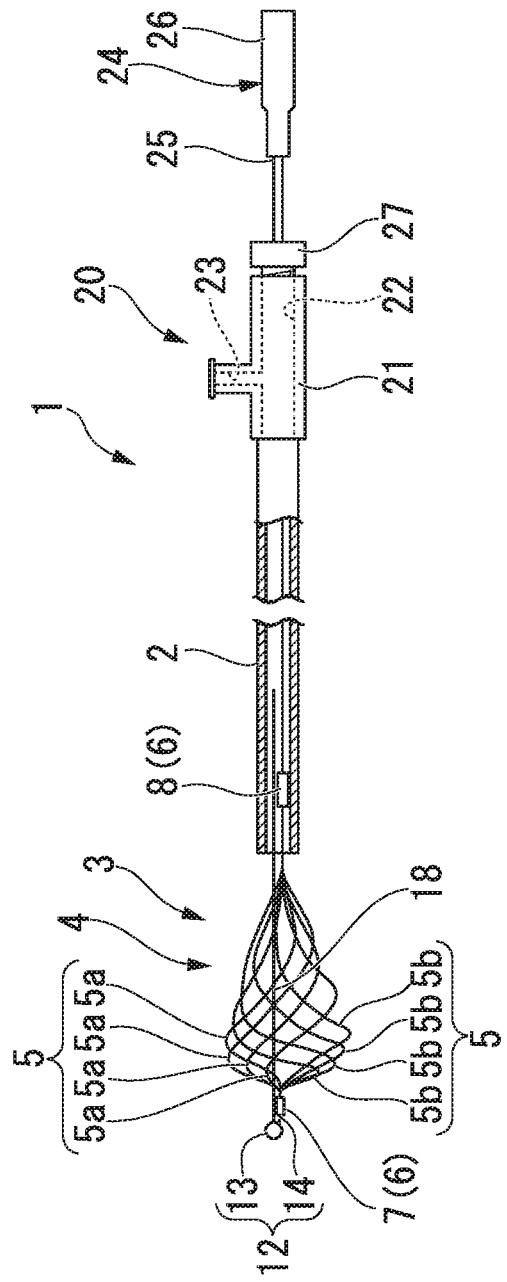
FIG. 6 is a view for showing an operation of the basket-type grasping forceps.
Figure 7:
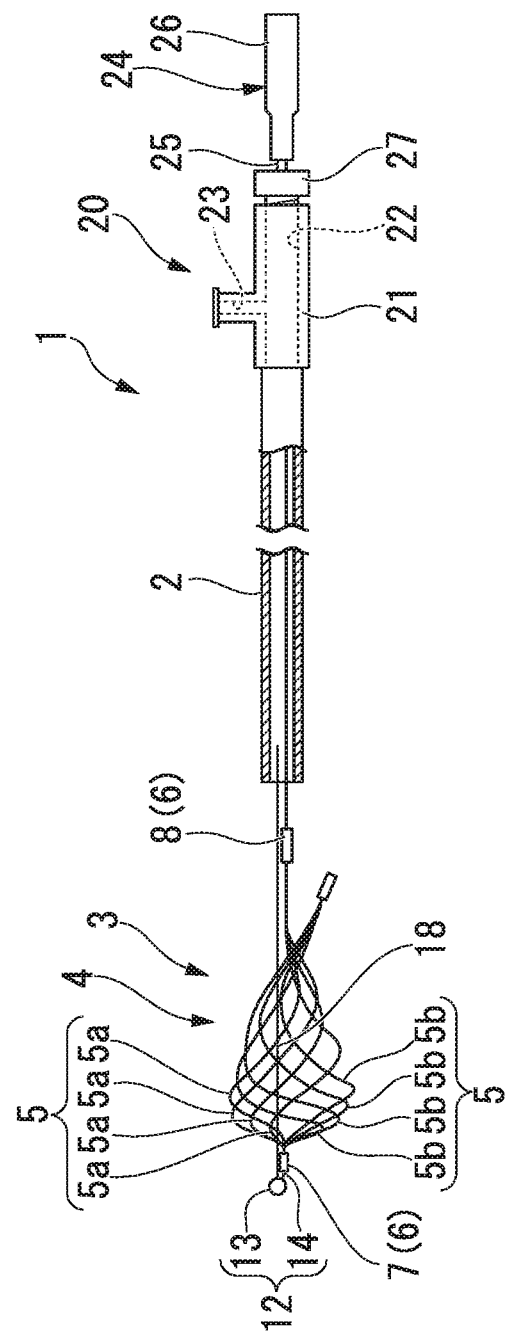
FIG. 7 is a view for showing an operation of the basket-type grasping forceps.

A first embodiment of the present invention will be described. FIG. 1 is a partial cross-sectional view showing a basket-type grasping forceps of the present embodiment. FIG. 2 is a side view showing a part of a basket section of the basket-type grasping forceps. FIG. 3 is a cross-sectional view taken along line A-A of FIG. 2. FIG. 4 is a cross-sectional view taken along line B-B of FIG. 2. FIG. 5 is a front view showing a part of the basket section. FIGS. 6 and 7 are views showing an operation of the basket-type grasping forceps 1.

The basket-type grasping forceps 1 of the present embodiment shown in FIG. 1 is a medical device that is inserted into an intracorporeal duct such as a bile duct and is intended to remove a foreign object.

The basket-type grasping forceps 1 has a sheath 2, a main body section 3 inserted into the sheath 2, and a manipulating section 20 fixed to the sheath 2.

The sheath 2 is a tubular member having flexibility. External dimensions of the sheath 2 are such as to be able to be inserted to move forward and backward relative to a treatment tool channel of an endoscope. A distal end of the sheath 2 has such hardness as to be able to fold a basket section 4 (to be described below) during use of the basket-type grasping forceps 1.

The main body section 3 is an elongated member that has distal and proximal ends and is inserted into the sheath 2. The main body section 3 has the basket section 4, a manipulating wire 19 connected to the basket section 4, and a center wire (a support member) 18 fixed to the basket section 4.

The basket section 4 is provided at a distal end of the manipulating wire 19 to collect a target. The basket section 4 is disposed at a distal side in the main body section 3, is spread in an approximate spindle shape to hold a foreign object, and is expandable and contractible. The basket section 4 has an approximately linear shape that can be housed in the sheath 2 in a contracted state.

The basket section 4 has a plurality of basket wires 5, a fixing member 6 for forming the plurality of basket wires 5 in an approximate spindle shape, and a tip member 12 that couples a distal end of the basket section 4 and a distal end of the center wire 18.

The plurality of basket wires 5 are disposed at a distal portion of the sheath 2 to form the approximate spindle shape in which a target to be collected in a body (for example, an intracorporeal foreign object such as a gallstone) is held inside. In the present embodiment, each of the plurality of basket wires 5 forms a spiral shape centered on a central line of the basket section 4. Moreover, all of the plurality of basket wires 5 have denser spiral pitches toward distal sides thereof. That is, a size of an opening made by the plurality of basket wires 5 is smallest at the distal end of the basket section 4, and is gradually increased toward a proximal side of the basket section 4. A distal portion of the basket section 4 is a dense portion 4a at which the basket wires 5 are disposed with such a gap as to catch a target. A proximal portion of the basket section 4 is a sparse portion 4b at which the basket wires 5 are disposed with such a gap as to be able to introduce a target into the basket section 4.

Materials of the plurality of basket wires 5 are materials having a restoring force with which the approximate spindle shape is maintained by the plurality of basket wires 5 in a state in which no external force is applied. In the present embodiment, each of the plurality of basket wires 5 is formed of a shape memory alloy. To be specific, the plurality of basket wires 5 in the present embodiment are made of a nickel titanium alloy. The basket section 4 of the present embodiment has eight basket wires 5. The number of basket wires 5 is not limited to eight, and may be properly selected depending on a shape of the basket section 4.

The fixing member 6 has a distal fixing member 7 that ties and fixes the basket wires 5 at a distal side of the basket section 4, and a proximal fixing member (a binding part) 8 that ties and fixes the basket wires 5 at the proximal side of the basket section 4. The distal fixing member 7 supports each of the basket wires 5 such that the distal end portions of the basket wires 5 are located on the same circumference, the center of which is on the central line of the basket section 4.

The distal fixing member 7 is a binding part that binds the plurality of basket wires 5 at the distal portion of the basket section 4. The distal fixing member 7 has a tubular shape. All of the basket wires 5 are inserted into the distal fixing member 7. The distal fixing member 7 and the basket wires 5 are fixed by a known fixing method such as adhesion, soldering, or welding.

A connecting part 14 (to be described below) is fixed to a distal end of the distal fixing member 7.

The proximal fixing member 8 shown in FIGS. 1 and 2 is a binding part that binds the plurality of basket wires 5 at the proximal portion of the basket section 4. The proximal fixing member 8 has a first binding part 9 to which at least one of the plurality of basket wires 5 (in the present embodiment, four first wires 5a) is fixed, and a second binding part 11 at which the remaining basket wires of the plurality of basket wires 5 (in the present embodiment, four second wires 5b) are fixed.

Proximal ends of the four first wires of the eight basket wires 5 are fixed to the first binding part 9 shown in FIGS. 2, 3, and 4, and the first binding part 9 is connected to the manipulating wire 19. The first binding part 9 and the basket wires 5 are fixed by a known fixing method such as adhesion, brazing, soldering, or welding.

The first binding part 9 has a holding part 9a that can hold the second binding part 11 in a state in which the second binding part 11 is in contact with the first binding part 9, and distal and proximal engaging parts 9b and 9c for engaging the second binding part 11 with respect to the first binding part 9. The four first wires 5a are arranged on and fixed to the first binding part 9 in a semicircular arc shape.

The holding part 9a regulates a space capable of housing the second binding part 11. In a state in which the second binding part 11 is inserted into the holding part 9a, the first binding part 9 and the second binding part 11 are integrally operated by the manipulating wire 19.

The distal engaging part 9b is disposed at a part of the distal side of the first binding part 9. A distal end portion of the second binding part 11 inserted into the holding part 9a is in contact with a surface directed to a proximal end side at the distal engaging part 9b. The distal engaging part 9b restricts movement of the second binding part 11 such that the second binding part 11 inserted into the holding part 9a of the first binding part 9 does not move to the distal side relative to the first binding part 9. The distal engaging part 9b is formed in a recessed shape to avoid the four second wires 5b such that it can be in contact with a distal end of the second binding part 11 and house all of the four second wires 5b. The surface directed to the proximal end side at the distal engaging part 9b is formed as a flat surface that does not restrict the movement of the second binding part 11 in a direction orthogonal to an axis of the manipulating wire 19.

The proximal engaging part 9c is disposed at a part of the proximal side of the first binding part 9. A proximal end portion of the second binding part 11 inserted into the holding part 9a is in contact with a surface directed to a distal side at the proximal engaging part 9c. The proximal engaging part 9c restricts the movement of the second binding part 11 such that the second binding part 11 inserted into the holding part 9a of the first binding part 9 does not move to the proximal side relative to the first binding part 9. The surface directed to the distal side at the proximal engaging part 9c is formed as a flat surface that does not restrict the movement of the second binding part 11 in the direction orthogonal to the axis of the manipulating wire 19.

Proximal ends of the basket wires 5 (the second wires 5b) different from the basket wires 5 (the first wires 5a) that are fixed to the first binding part 9 among the plurality of basket wires 5 are fixed to the second binding part 11. In the present embodiment, the proximal end of each of the second wires 5b is fixed to the distal end of the second binding part 11. The four second wires 5b are arranged on and fixed to the second binding part 11 in a semicircular arc shape.

As shown in FIGS. 2 and 3, in a state in which the first binding part 9 and the second binding part 11 are combined, the second binding part 11 is inserted into the holding part 9a of the first binding part 9. At this point, the first wires 5a arranged in a semicircular arc shape and the second wires 5b arranged in a semicircular arc shape are arranged in a circular shape as a whole.

The tip member 12 shown in FIG. 1 has a tip main body 13 in which a distal end thereof has a curved shape, and the wire-like connecting part 14 that couples the tip main body 13 and the distal fixing member 7.

The tip main body 13 is fixed to the distal end of the distal fixing member 7 via the connecting part 14.

The center wire 18 shown in FIGS. 1 and 5 is connected to the distal end of the basket section 4, and is inserted into the sheath 2 via the inside of the basket section 4. The distal end of the center wire 18 is fixed to a proximal end of the tip member 12. The center wire 18 is adapted to pass through the inside of the basket section 4 at a position that is offset from the distal fixing member 7 inside of the basket section 4 in an outer circumferential direction relative to the central line of the basket section 4.

In the dense portion 4a of the basket section 4, the center wire 18 is disposed at a position that is closer to the basket wires (the first wires 5a) that are fixed to the first binding part 9 among the basket wires 5 than to the basket wires (the second wires 5b) that are fixed to the second binding part 11 among the basket wires 5. For this reason, when a foreign object such as a calculus is caught in the dense portion 4a of the basket section 4, a relatively wide space which the foreign object enters is secured at the near side to the second wires 5b.

A proximal region of the center wire 18 is disposed inside the sheath 2. The proximal end of the center wire 18 extends to the proximal side relative to the proximal fixing member 8.

The manipulating wire 19 shown in FIG. 1 is fixed to the basket section 4 and is disposed at the proximal side of the basket section 4. The manipulating wire 19 and the basket section 4 are fixed by a known fixing method such as adhesion, brazing, soldering, swaging, or welding. The manipulating wire 19 extends to the manipulating section 20 through the inside of the sheath 2.

The manipulating section 20 shown in FIG. 1 is provided at the proximal end of the sheath 2 to displace the manipulating wire 19 and the center wire 18 forward and backward relative to the sheath 2. The manipulating section 20 is provided at the proximal end of the sheath 2.

The manipulating section 20 has a manipulation main body 21, a slider 24, and an adjusting mechanism 27.

The manipulation main body 21 is fixed to the proximal end of the sheath 2. The manipulation main body 21 has a first port 22 into which a part of the slider 24 for displacing the manipulating wire 19 forward and backward is inserted, and a second port 23 that communicates with the first port 22 in the manipulation main body 21 and is open to the outside of the manipulation main body 21.

The first port 22 is a port in which a shaft 25 (to be described below) can move forward and backward in a water-proof state.

The second port 23 is a port that can connect to, for example, a syringe for sending a liquid such as a contrast agent or washing water. The second port 23 communicates with the sheath 2 through the inside of the manipulation main body 21. When a liquid is injected from the second port 23 in a state in which the first port 22 is in a water-proof state, the liquid flows into the sheath 2 and is discharged from an opening of the distal end side of the sheath 2.

The slider 24 has the shaft 25 that is fixed to the proximal end of the manipulating wire 19, and a grip 26 disposed at a proximal end of the shaft 25.

The shaft 25 is a hard member, and is formed in a pipe or rod shape. The manipulating wire 19 and the shaft 25 may be fixed by a known fixing method of adhesion, brazing, soldering, or welding.

The grip 26 is a member that is formed to be larger than a contour of the shaft 25 such that it is easy for an operator of the basket-type grasping forceps 1 to hold the grip 26. The grip 26 may have slip resistance as necessary.

The adjusting mechanism 27 is connected to a proximal end portion of the manipulation main body 21. The adjusting mechanism 27 is a tubular member that has a through-hole into which the shaft 25 is inserted. The adjusting mechanism 27 is movable relative to the manipulation main body 21 to be projected and retracted. Moreover, the adjusting mechanism 27 can be fixed to the manipulation main body 21 at two positions that are different from each other in an amount of projection from the manipulation main body 21.

The adjusting mechanism 27 switches between a state in which the movement of the manipulating wire 19 is restricted such that the first binding part 9 and the second binding part 11 move forward and backward in the sheath 2 (see FIG. 1) and a state in which the movement of the manipulating wire 19 is allowed up to a position at which the first binding part 9 and the second binding part 11 are exposed outside the sheath 2 (see FIGS. 6 and 7), and adjusts an amount of forward/backward movement of the manipulating wire 19.

As a mechanism for fixing the adjusting mechanism 27 to the manipulation main body 21 or allowing the adjusting mechanism 27 to move relative to the manipulation main body 21, a known constitution may be adequately selected and adopted. For example, the adjusting mechanism 27 and the manipulation main body 21 may be screwed together as shown in FIG. 1, or the adjusting mechanism 27 may be turned relative to the manipulation main body 21 as shown in FIGS. 1 and 6, and an amount of projection from the adjusting mechanism 27 may be changed. As another example, the manipulation main body 21 may have a stopper structure (not shown) which is engaged with the adjusting mechanism 27 so as to restrict the movement of the adjusting mechanism 27 relative to the manipulation main body 21. When this stopper structure is, for example, released manually, the adjusting mechanism 27 can move relative to the manipulation main body 21.

Figure 8:
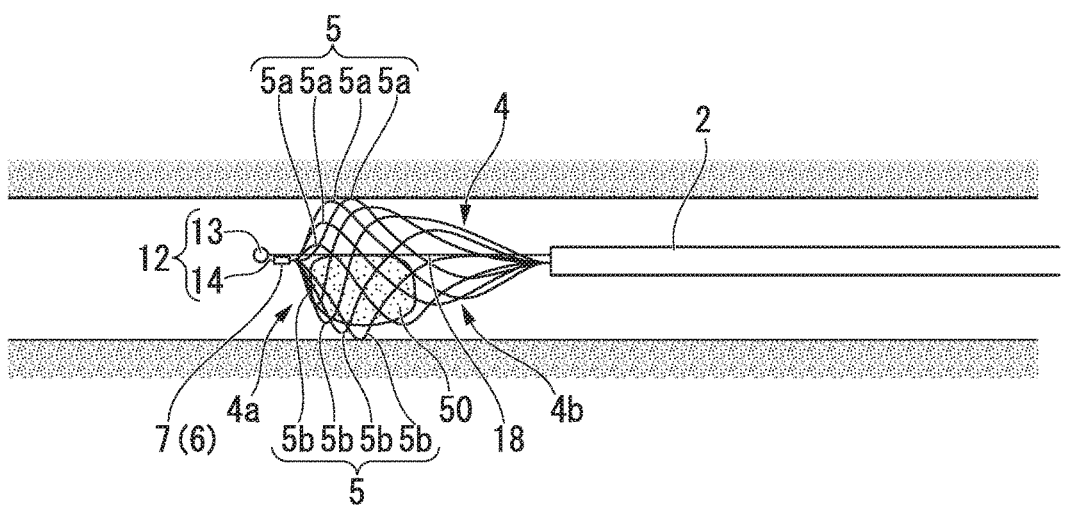
FIG. 8 is a schematic view showing an example of stone collection using the basket-type grasping forceps.
Figure 13:
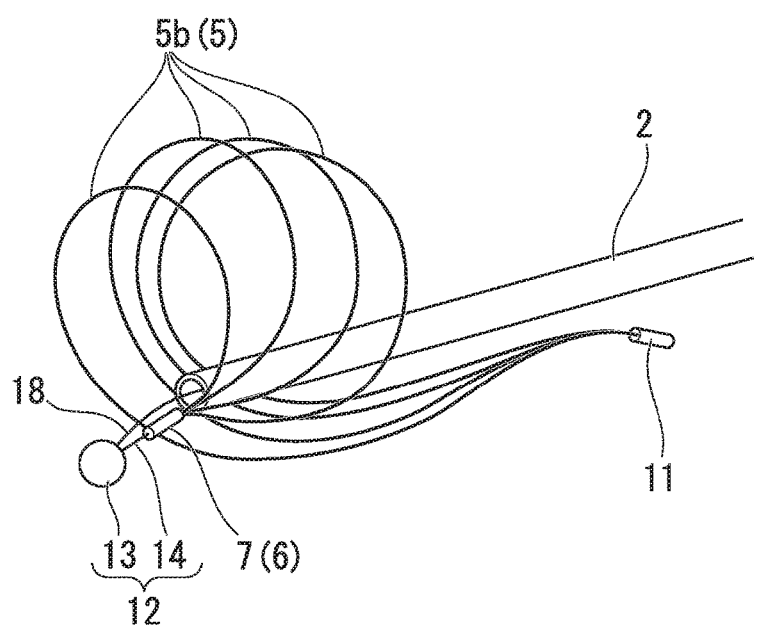
FIG. 13 is a perspective view showing an operation of the basket section by the basket-type grasping forceps.
Figure 14:
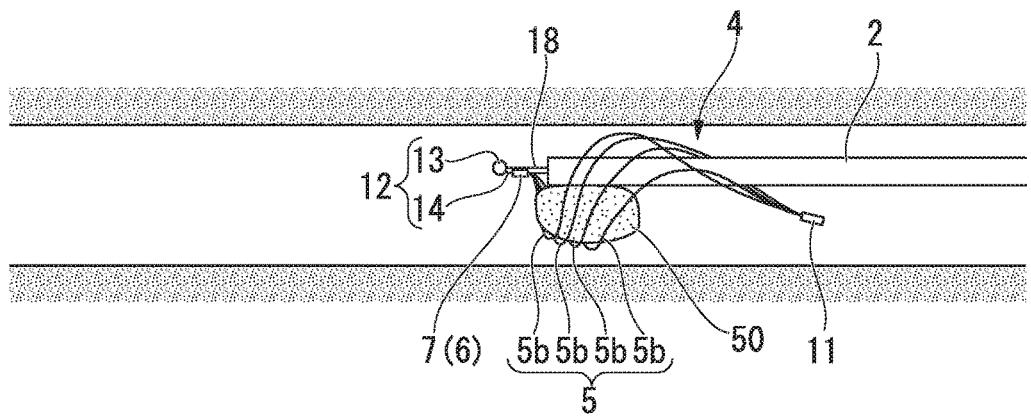
FIG. 14 is a schematic view showing the process of releasing a calculus during the stone collection using the basket-type grasping forceps.
Figure 15:
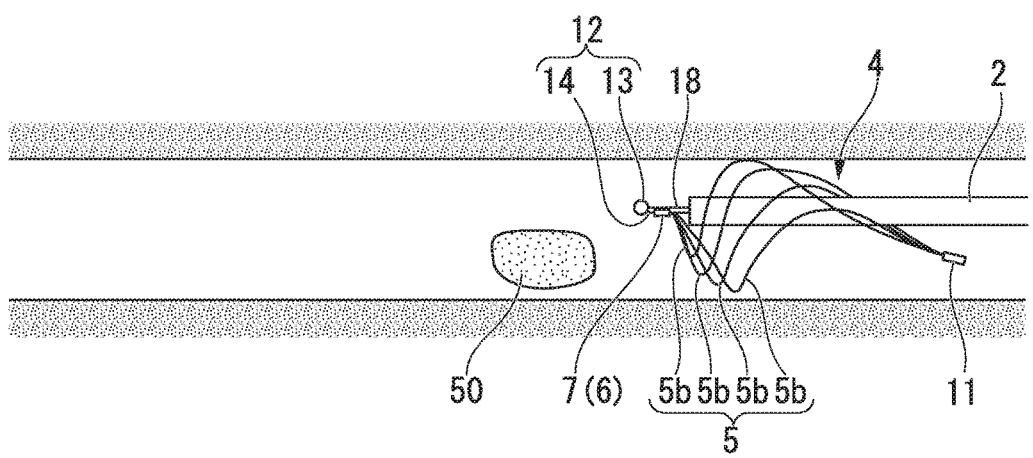
FIG. 15 is a schematic view showing the process of releasing a calculus during the stone collection using the basket-type grasping forceps

Next, an operation of the basket-type grasping forceps 1 of the present embodiment will be described. FIG. 8 is a schematic view showing an example of stone collection using the basket-type grasping forceps 1. FIGS. 9 to 12 are schematic views showing a process of releasing a calculus during the stone collection using the basket-type grasping forceps 1. FIG. 13 is a perspective view showing an operation of the basket section 4 by the basket-type grasping forceps 1. FIGS. 14 and 15 are schematic views showing the process of releasing a calculus during the stone collection using the basket-type grasping forceps 1.

As shown in FIG. 8, the basket-type grasping forceps 1 of the present embodiment is inserted into a duct such as a bile duct in the body of a patient through an endoscope channel in a state in which the basket section 4 is stored in the sheath 2 like an ordinary basket type medical treatment tool.

In a typical use mode in which a foreign object is introduced into the basket section 4, as shown in FIG. 1, the adjusting mechanism 27 is fixed at a position at which it maximally protrudes from the manipulation main body 21 to be in a state in which the movement of the manipulating wire 19 is restricted such that the first binding part 9 and the second binding part 11 move forward and backward in the sheath 2. When the basket section 4 protrudes from the sheath 2 to the distal side in the duct due to a forward movement manipulation of the slider 24 shown in FIG. 1, the basket section 4 is expanded by an elastic force of the basket wires 5. At this point, the first binding part 9 and the second binding part 11 are enclosed by an inner circumferential surface of the sheath 2 as shown in FIGS. 3 and 4 in a state in which the second binding part 11 is inserted into the holding part 9a of the first binding part 9 as shown in FIG. 2. For this reason, the first binding part 9 and the second binding part 11 integrally move forward and backward in the sheath 2 without being separated inside the sheath 2.

As shown in FIG. 8, an operator introduces a foreign object 50 such as a calculus into the expanded basket section 4, and then displaces the slider 24 (see FIG. 1) to the proximal side. Thereby, the basket section 4 is reduced in diameter, and the foreign object 50 can be firmly held in the basket. The foreign object introduced into the basket section 4 gathers at the dense portion 4a of the basket section 4 in the basket section 4, specifically in the vicinity of the second wires 5b that are a portion secured to be relatively wide at the dense portion 4a of the basket section 4 (see FIG. 8). In this state, the operator extracts the basket section 4 from the duct such as the bile duct, and then removes the basket-type grasping forceps 1 from the inside of the body of the patient along with the endoscope. Thereby, the foreign object 50 is collected.

Depending on a size or the like of the foreign object 50, the basket-type grasping forceps 1 sometimes cannot be removed from a duct with the foreign object 50 held in the basket section 4. In this case, the basket wires 5 are maximally expanded by completely exposing the basket section 4 from the opening of the distal end of the sheath 2, and thereby the foreign object 50 can be released from a gap between the basket wires 5 to the outside of the basket. However, when the foreign object 50 cannot be released even in the state in which the basket wires 5 are maximally expanded, the basket section 4 can be intentionally broken by the following manipulation.

To break the basket section 4 in the present embodiment, the adjusting mechanism 27 is displaced relative to the manipulation main body 21 such that the amount of projection of the adjusting mechanism 27 from the manipulation main body 21 is reduced, as shown in FIG. 6. Due to this manipulation, the movement of the manipulating wire 19 is allowed up to a position at which the first binding part 9 and the second binding part 11 are exposed to the outside of the sheath 2. As shown in FIG. 7, when the first binding part 9 and the second binding part 11 are both exposed to the outside of the sheath 2, the first binding part 9 and the second binding part 11 are released from holding by the inner circumferential surface of the sheath 2, and can be separated from each other. For this reason, when the first binding part 9 and the second binding part 11 are both exposed to the outside of the sheath 2, the second binding part 11 is separated from the first binding part 9.

Figure 9:
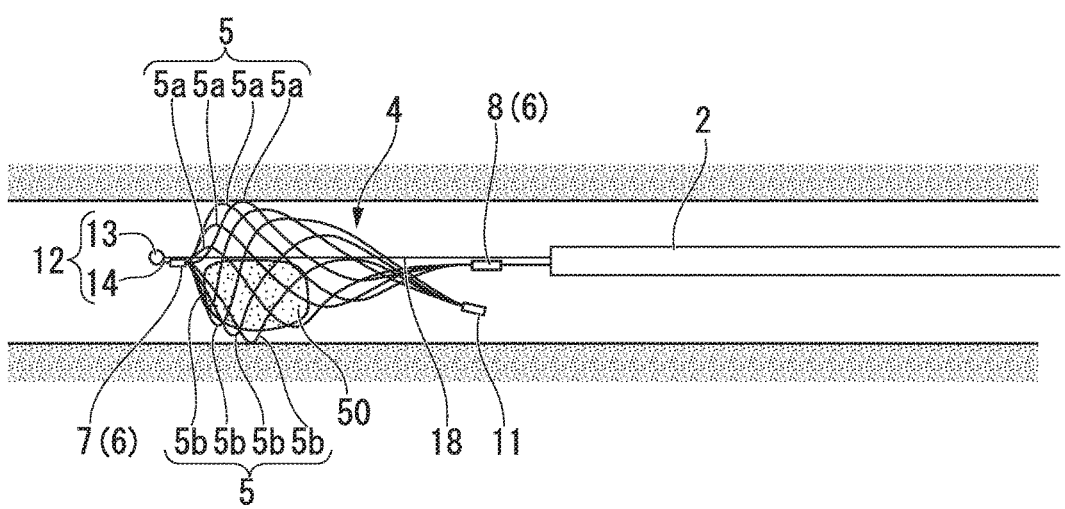
FIG. 9 is a schematic view showing a process of releasing a calculus during the stone collection using the basket-type grasping forceps.

As shown in FIG. 9, when the second binding part 11 is separated from the first binding part 9, the first wires 5a and the second wires 5b, which are arranged in a circular shape as a whole, are each separated as four wires arranged in a semicircular arc shape. For this reason, the first wires 5a and the second wires 5b cannot maintain the shape of the basket section 4, and the shape of the basket section 4 does not have the approximate spindle shape.

Since the first wires 5a are configured such that the distal portions thereof are held by the center wire 18 and the proximal portions thereof are held by the manipulating wire 19, the first wires 5a are maintained in nearly the same shape as before the separation of the second binding part 11 with no change from a shape formed by a part of the approximate spindle shape.

While distal portions of the second wires 5b are held by the center wire 18, the second binding part 11 is separated from the first binding part 9, and thereby the second wires 5b is released from holding by the manipulating wire 19. For this reason, as shown in FIG. 10, the second wires 5b are deformed to form a loop shape by an elasticity of the second wires 5b themselves.

Figure 10:
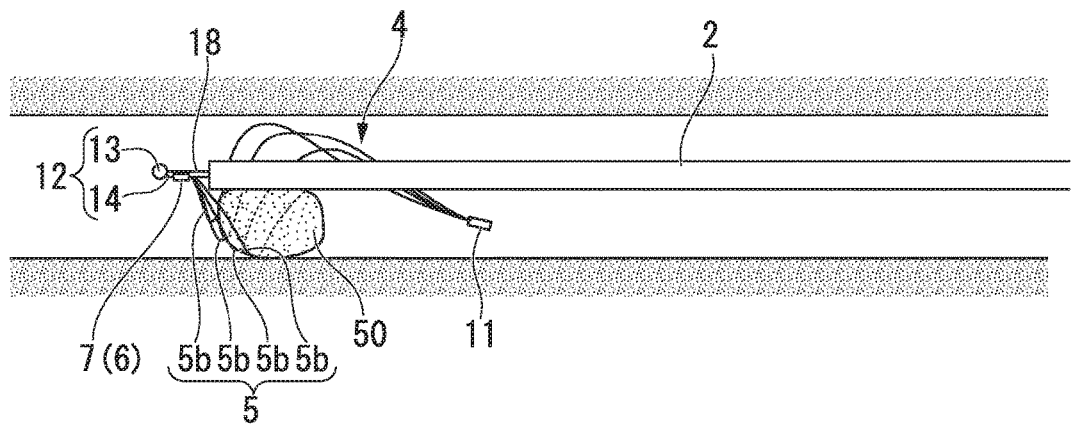
FIG. 10 is a schematic view showing the process of releasing a calculus during the stone collection using the basket-type grasping forceps.
Figure 11:
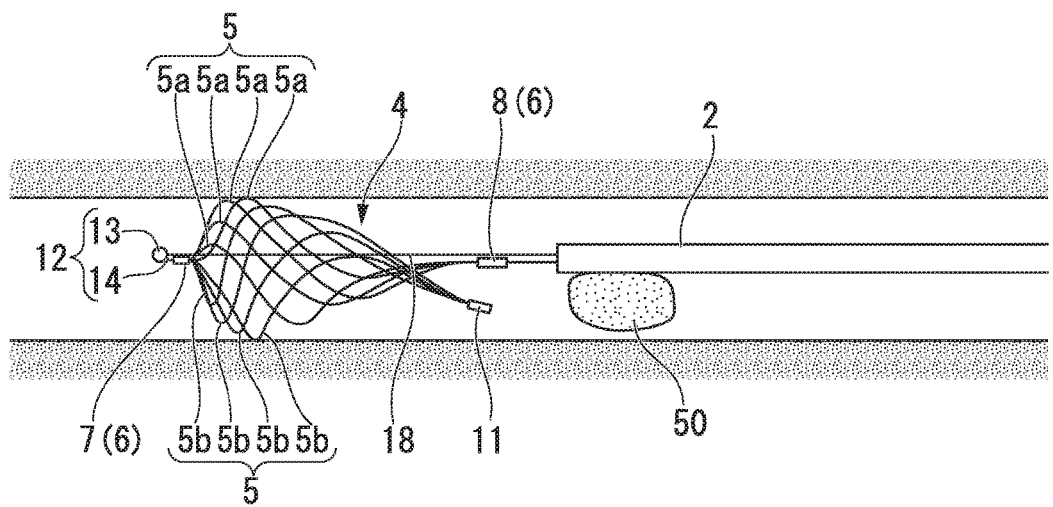
FIG. 11 is a schematic view showing the process of releasing a calculus during the stone collection using the basket-type grasping forceps.
Figure 12:
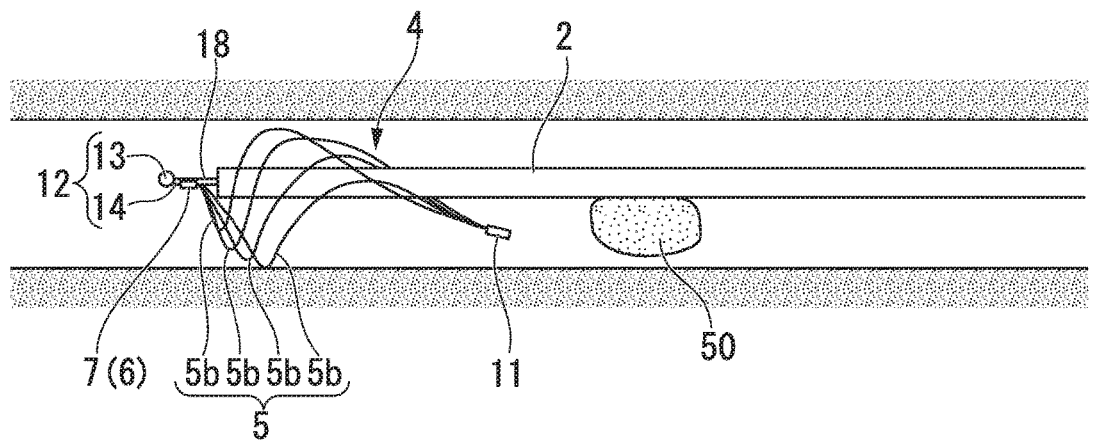
FIG. 12 is a schematic view showing the process of releasing a calculus during the stone collection using the basket-type grasping forceps.

Subsequently, the manipulating wire 19 is pulled back to the proximal side, and the first wires 5a of the basket wires 5 are drawn into the sheath 2 as shown in FIG. 10. Then, in the present embodiment, since half of the total basket wires 5 are disposed in the sheath 2, the foreign object 50 inside the basket section 4 can be extracted from the proximal side of the basket section 4 to the outside of the basket section 4.

The manipulating wire 19 is extruded to the distal side again to displace the basket section 4 (see FIG. 11) or the manipulating section 20 itself is extruded to the distal side to extract the foreign object 50 from the proximal side of the basket section 4 to the outside of the basket section 4.

In a state in which the foreign object 50 is released from the basket section 4 and then the basket section 4 completely leaves the sheath 2, the basket section 4 interferes with the foreign object 50, and the basket-type grasping forceps 1 is difficult to extract from the body. For this reason, in the present embodiment, the foreign object 50 is released from the basket section 4, and then the manipulating wire 19 is displaced to the proximal side. Thereby, the first wires 5a are displaced into the sheath 2.

Since the foreign object 50 is released from the basket section 4, the second wires 5b disposed outside the sheath 2 have loop shapes in which openings are directed to each of the distal and proximal sides of the basket section 4 by the elasticity of the second wires 5b themselves (see FIG. 13). At this point, open portions of the loops caused by the second wires 5b can be used as a passage through which the foreign object 50 introduced into the basket section 4 passes (see FIG. 14). For this reason, when the second binding part 11 is separated from the first binding part 9 and then the basket section 4 is pulled back to the proximal side, the foreign object present in the basket section 4 passes through the openings of the loops caused by the second wires 5b, and remains in the duct as shown in FIG. 15. As a result, the foreign object 50 inside the basket section 4 is released from the basket section 4, and the basket-type grasping forceps 1 is able to be removed from the duct.

After the breaking of the basket section 4, the basket-type grasping forceps 1 is not reused. Moreover, since the basket section 4 is broken to leave the foreign object in the duct, the foreign object is collected by another procedure capable of collecting the foreign object. For example, the foreign object is divided into small pieces using a crushing basket, or the foreign object is removed by a laparotomy.

To release a foreign object from a basket in a duct at a conventional basket-type grasping forceps, a method of, for example, introducing a crushing device or the like into the body to crush the foreign object is required.

However, introducing the crushing device or the like into the body only for the purpose of releasing the foreign object held in the basket from inside the duct is inefficient.

The basket-type grasping forceps 1 of the present embodiment allows a movable range of the manipulating wire 19 to be changed by the adjusting mechanism 27. For this reason, an operation to break the basket section 4 is made possible by changing the movable range of the manipulating wire 19 using the adjusting mechanism 27 such that the first binding part 9 and the second binding part 11 leave the sheath 2. As a result, there is no need to apply a great force to break the basket section 4, and a foreign object can be easily released from the basket section 4 only by displacing the manipulating wire 19 such that the first binding part 9 and the second binding part 11 leave the sheath 2.

Moreover, as the adjusting mechanism 27 is provided, the first binding part 9 and the second binding part 11 are held inside the sheath 2 by the inner surface of the sheath 2, and are not separated during an operation to introduce a foreign object into the basket section 4. As a result, the basket section 4 is not unintentionally broken in a process of introducing a foreign object into the basket section 4.

(Second Embodiment)

Figure 16:
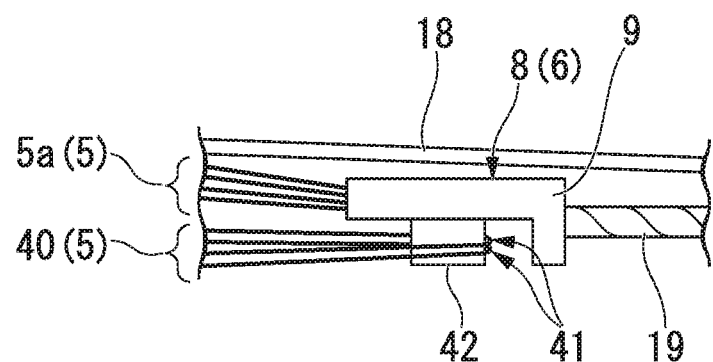
FIG. 16 is a side view showing a part of a basket section in a basket-type grasping forceps of a second embodiment of the present invention.

Next, a second embodiment of the present invention will be described. In each embodiment following the present embodiment, the same components as in the first embodiment are given the same reference signs, and description overlapping that of the first embodiment will be omitted. FIG. 16 is a side view showing a part of a basket section in a basket-type grasping forceps of the present embodiment.

In place of the second wires 5b described in the first embodiment, the basket-type grasping forceps of the present embodiment has second wires 40 having folds 41 at proximal end portions thereof.

In the basket-type grasping forceps of the present embodiment, in place of the holding part 9a, a first binding part 9 has a projection 42 on which the folds 41 of the second wires 40 are caught.

In the present embodiment, two wires are respectively folded at the folds 41, and thereby the second wires 40 constitute the same basket section 4 as in the first embodiment. The folds 41 of the two second wires 40 couple the second wires 40 to the first binding part 9.

In a state in which the folds 41 of the second wires 40 are hooked on the projection 42 of the first binding part 9, when the projection 42 and the folds 41 are together disposed in a sheath 2, the second wires 40 do not leave the projection 42 in the sheath 2 (see FIG. 1), and the basket section 4 can maintain an approximate spindle shape. In the state in which the folds 41 of the second wires 40 are hooked on the projection 42 of the first binding part 9, when the projection 42 and the folds 41 leave the sheath 2, the folds 41 are unhooked from the projection 42, and the second wires 40 are deformed in a loop shape having openings through which a foreign object can pass like in the first embodiment.

In the present embodiment, like in the first embodiment, there is no need to apply an excessive force to break the basket section 4.

Although the embodiments of the present invention have been described above in detail with reference to the drawings, the specific constitution is not limited to these embodiments and also includes a change in design and so on without departing from the scope of the present invention.

Moreover, the components represented in each of the embodiments and modifications thereto can be configured by an appropriate combination thereof.

While preferred embodiments of the present invention have been described, the present invention is not limited to the embodiments. Additions, omissions, substitutions, and other variations may be made to the present invention without departing from the spirit and scope of the present invention. The present invention is not limited by the above description, but by the appended claims.

What is claimed is:

1. A basket-type grasping forceps comprising:
   a sheath;
   a manipulating wire inserted into the sheath;
   a plurality of basket wires including a plurality of first wires and a plurality of second wires, the plurality of basket wires being projected from a distal portion of the sheath, the plurality of basket wires forms a basket section configured to hold a target;
   a first binder to which proximal ends of the plurality of first wires are fixed in a proximal side of the plurality of basket wires, the plurality of first wires fixed to the first binder being arranged in a semicircular arc shape, the first binder being connected to the manipulating wire, the first binder being configured to move between an inside of the sheath and an outside of the sheath; and
   a second binder to which proximal ends of the plurality of second wires are fixed, the plurality of second wires fixed to the second binder being arranged in a semicircular arc shape, the second binder being configured to be: (i) held by the first binder in the sheath, and (ii) separated from the manipulating wire by separating the second binder from the first binder in a state in which the second binder is disposed at the outside of the sheath, the plurality of second wires being deformed to form a loop shape by an elasticity of the plurality of second wires by the plurality of basket wires in response to separating from the first binder, wherein:
the plurality of second wires is separated from the plurality of first wires; and
a first loop is formed by the plurality of second wires in a distal end of the basket section, and a second loop is formed by the plurality of second wires in a proximal end of the basket section in a state where the plurality of first wires moves in the sheath.

2. The basket-type grasping forceps according to claim 1, wherein the basket section includes:
a dense portion at which the plurality of basket wires are disposed in a spiral shape at an interval which enables capture of the target at a distal end side of the basket section; and
a sparse portion at which the plurality of basket wires are disposed in a spiral shape at an interval which enables introduction of the target into the basket section at a proximal end side of the basket section.

3. The basket-type grasping forceps according to claim 1, wherein:
the first binder has a distal engaging part disposed closer to a distal end of the sheath than a distal end of the second binder in a state in which the second binder is in the sheath; and
the distal engaging part includes a first contact surface facing towards a proximal side of the sheath such that the first contact surface is configured to engage the second binder.

4. The basket-type grasping forceps according to claim 3, wherein:
the first binder has a proximal engaging part disposed closer to a proximal end of the sheath than the proximal end of the second binder in the state in which the second binder is in the sheath; and
the proximal engaging part including a second contact surface facing towards a distal side of the sheath such that the second contact surface is configured to engage the second binder.

5. The basket-type grasping forceps according to claim 1, further comprising a stopper configured to restrict movement of the manipulating wire so that the stopper is configured to switch between a state in which movement of the manipulating wire is restricted such that the first binder and the second binder move forward and backward in the sheath and a state in which the movement of the manipulating wire is allowed up to a position at which the first binder and the second binder are exposed outside the sheath.

6. The basket-type grasping forceps according to claim 1, wherein the basket section includes a support member connected to distal ends of the plurality of basket wires, the support member being at least partially inserted into the sheath.

7. The basket-type grasping forceps according to claim 6, wherein:
the basket section includes:
a dense portion at which the plurality of basket wires are disposed in a spiral shape at an interval which enables capture of the target at a distal end side of the basket section; and
a sparse portion at which the plurality of basket wires are disposed in a spiral shape at an interval which enables introduction of the target into the basket section at a proximal end side of the basket section; and the support member is disposed in the dense portion of the basket section at a position that is closer to the plurality of basket wires fixed to the first binder among the plurality of basket wires than to the plurality of basket wires fixed to the second binder among the plurality of basket wires.

8. The basket-type grasping forceps according to claim 1, wherein the second binder is configured to be inserted into the first binder.

9. The basket-type grasping forceps according to claim 1, wherein:
the plurality of first wires are fixed to the first binder in a state where the plurality of first wires are inserted into the first binder, and
the plurality of second wires are fixed to the second binder in a state where the plurality of second wires are inserted into the second binder.

10. The basket-type grasping forceps according to claim 1, wherein:
the plurality of first wires fixed to the first binder are arranged in the semicircular arc shape about a central axis of the basket section; and
the plurality of second wires fixed to the second binder are arranged in the semicircular arc shape about the central axis of the basket section.

11. The basket-type grasping forceps according to claim 10, wherein:
the first binder is connected to the manipulating wire; and
the second binder is configured to be separated from the manipulating wire when the second binder is separated from the first binder.

12. A basket-type grasping forceps comprising:
a sheath;
a manipulating wire inserted into the sheath;
a basket section configured to hold a target, and the basket section is formed by a plurality of basket elastic wires, the plurality of basket elastic wires including a plurality of first wires and a plurality of second wires, the plurality of first wires being projected from a distal portion of the sheath, the plurality of basket elastic wires extending in a helical shape about a central axis of the basket section;
a distal fixing member that is fixed to a distal end part of the basket elastic wires;
a first binder to which proximal ends of the plurality of first wires are fixed in a proximal side of the plurality of basket elastic wires, the first binder being connected to the manipulating wire, the first binder being configured to move between an inside of the sheath and an outside of the sheath; and
a second binder to which proximal ends of the plurality of second wires are fixed, second binder being configured to be: (i) held by the first binder in the sheath, and (ii) separated from the manipulating wire by separating the second binder from the first binder in a state in which the second binder is disposed at the outside of the sheath, the second binder moving towards the distal fixing member by separating the second binder from the first binder, wherein:
the plurality of second wires is separated from the plurality of first wires; and
a first loop is formed by the plurality of second wires in a distal end of the basket section, and a second loop is formed by the plurality of second wires in a proximal end of the basket section.

13. The basket-type grasping forceps according to claim 12, wherein:

the plurality of first wires fixed in the first binder are arranged in a semicircular arc shape about a central axis of the basket section; and the plurality of second wires fixed in the second binder are arranged in a semicircular arc shape about the central axis of the basket section.

14. The basket-type grasping forceps according to claim 12, wherein the basket section includes:

a dense portion at which the plurality of basket elastic wires are disposed at an interval which enables capture of the target at a distal end side of the basket section; and a sparse portion at which the plurality of basket elastic wires are disposed at an interval which enables introduction of the target into the basket section at a proximal end side of the basket section.

15. A basket-type grasping forceps comprising:

a sheath;

a manipulating wire inserted into the sheath;

a basket section configured to hold a target, and the basket section is formed by a plurality of basket elastic wires, the plurality of basket elastic wires including a plurality of first wires and a plurality of second wires, the plurality of first wires being projected from a distal portion of the sheath;

a first binder to which proximal ends of at least of first wires are fixed in a proximal side of the plurality of basket elastic wires, the first binder being connected to the manipulation wire, the first binder being configured to move between an inside of the sheath and an outside of the sheath; and a second binder to which proximal ends of at least of second wires are fixed, second binder being configured to be: (i) held by the first binder in the sheath, and (ii) separated from the manipulating wire by separating the second binder from the first binder in a state in which the second binder is disposed at the outside of the sheath, wherein:

at least one of the plurality of second wires is covered by the second binder;

the plurality of second wires is separated from the plurality of first wires; and a first loop is formed by the plurality of second wires in a distal end of the basket section, and a second loop is formed by the plurality of second wires in a proximal end of the basket section in a state where the plurality of first wires moves in the sheath.

16. The basket-type grasping forceps according to claim 15, wherein:

the plurality of first wires fixed to the first binder are arranged in a semicircular arc shape about a central axis of the basket section; and the plurality of second wires fixed to the second binder are arranged in a semicircular arc shape about the central axis of the basket section.

17. The basket-type grasping forceps according to claim 15, wherein the plurality of basket elastic wires extend in a helical shape.

* * * * *